United States Patent [19]

Bouzard et al.

[11] 4,322,424

[45] Mar. 30, 1982

[54] CRYSTALLINE GLUCOCONATE SALT OF M-AMSA AND COMPOSITIONS CONTAINING SAME

[75] Inventors: Daniel Bouzard, Franconville; Claude Perol, Paris; Jacques Stemer, Paris; Abraham Weber, Paris, all of France; Edmund S. Granatek, Syracuse, N.Y.

[73] Assignee: Bristol-Myers Company, New York, N.Y.

[21] Appl. No.: 194,350

[22] Filed: Oct. 17, 1980

Related U.S. Application Data

[63] Continuation of Ser. No. 114,809, Jan. 24, 1980, abandoned.

[51] Int. Cl.$^3$ .................... C07D 219/10; A61K 31/47
[52] U.S. Cl. ...................................... 424/257; 546/106
[58] Field of Search ......................... 546/106; 424/257

[56] References Cited

U.S. PATENT DOCUMENTS 3,839,344  10/1974  Sherlock ............................ 546/318
4,258,191   3/1981  Dubicki et al. ..................... 424/257

OTHER PUBLICATIONS

Cain et al., European Journal of Chemistry, vol. 10, pp. 539-549, Pub. in Great Britain, (1974).

The Condensed Chemical Dictionary, Ninth Edition, Pub. Van Nostrand Reinhold Company, pp. 414-415, 1977.

Lachman et al., The Theory and Practice of Industrial Pharmacy, Second Edition, pp. 521-524, (1976).

*Primary Examiner*—Alan L. Rotman
*Attorney, Agent, or Firm*—David M. Morse

[57] ABSTRACT

The invention concerns a crystalline monogluconate salt of the antitumor agent 4'-(9-acridinylamino)-methanesulfon-m-anisidide and compositions comprising mixtures of such salt with an organic acid selected from gluconic acid, gluconolactone or mixtures thereof. The novel salt and compositions are characterized in having unexpectedly high water-solubility.

7 Claims, 2 Drawing Figures

INFRARED SPECTRUM OF m-AMSA, GLUCONATE SALT (KBr)

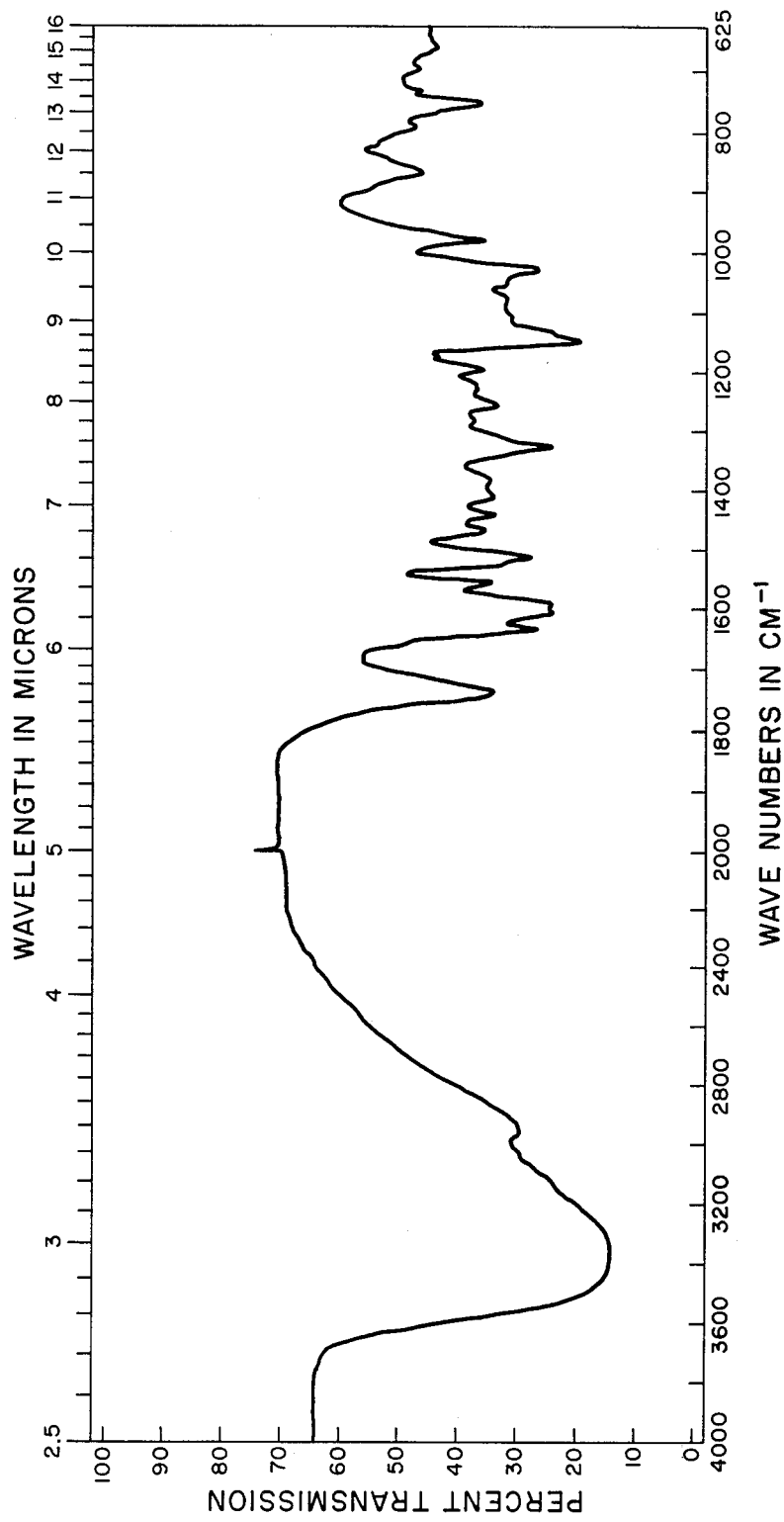

CRYSTALLINE GLUCOCONATE SALT OF M-AMSA AND COMPOSITIONS CONTAINING SAME

This is a continuation of application Ser. No. 114,809, filed Jan. 24, 1980, now abandoned.

BACKGROUND OF THE INVENTION

1. Field of the Invention

The novel acid addition salt and compositions of the present invention possess the advantageous antitumor properties of the known free base compound and in addition have unexpectedly high water-solubility, thus allowing preparation of useful clinical dosage forms for intravenous administration.

2. Description of the Prior Art

The acridine derivative m-AMSA [4'-9-acridinylamino) methanesulfon-m-anisidide] has been reported by Cain, et al. in Europ. J. Cancer 10:539–549 (1974) to possess significant antitumor activity in animal tumor systems. Since then, this compound has been subjected to clinical evaluation with very promising initial results.

When an antitumor agent such as m-AMSA is employed for human clinical use, it is recognized that solubility of the agent is often the controlling factor in determining route of administration and dosage forms. For instance, a water-soluble substance can be generally administered intravenously whereas a water-insoluble material is limited to other forms of parenteral administration such as intramuscular and subcutaneous. A therapeutic agent having water solubility also facilitates preparation of oral and non-intravenous parenteral dosage forms for human administration. Thus, it is decidedly advantageous if a therapeutic agent is water-soluble, particularly when one considers that the most direct route for achieving therapeutic blood levels of a drug within the human body is by intravenous administration.

The free base form of m-AMSA has very limited solubility in water and thus cannot be used as a dosage form for intravenous administration. Attempts have been made to prepare acid addition salts to overcome this solubility problem, but the reported monohydrochloride and monomethane-sulfonate salts also proved insufficiently water-soluble for clinical use. The formulation presently in clinical use consists of two sterile liquids combined just prior to use. A solution of m-AMSA in anhydrous N,N-dimethylacetamide is contained in an ampule. A separate vial contains an aqueous lactic acid solution for use as diluent. When mixed the resulting m-AMSA solution is administered by i.v. infusion.

While the present clinical formulation provides an intravenous dosage form, it suffers from several disadvantages. In addition to the obvious difficulties in preparing and administering the dosage form, it contains dimethylacetamide as a vehicle. Dimethylacetamide has been reported to show various toxic symptoms in animals and may thus prove to be unacceptable or undesirable as a pharmaceutical vehicle.

It is accordingly an object of the present invention to provide water-soluble, stable, therapeutically acceptable forms of m-AMSA which can be administered intravenously (as well as by other routes) and which do not contain or require dimethylacetamide as a pharmaceutical vehicle. This object as well as other features and advantages of the invention will be readily apparent to those skilled in the art from the disclosure set out below.

SUMMARY OF THE INVENTION

In one aspect the present invention provides a novel water-soluble acid addition salt of m-AMSA which upon reconstitution with sterile water or a sterile aqueous vehicle can be administered intravenously and which does not have the disadvantages associated with the known intravenous forms of this agent. More particularly, there is provided the crystalline monogluconate salt of m-AMSA.

In another aspect the invention provides a stable, solid, water-soluble composition for reconstitution with water or an aqueous vehicle as a stable solution of m-AMSA, said composition comprising a mixture of about one mole of m-AMSA monogluconate salt per one to three moles of an organic acid (or precursor thereof) selected from gluconic acid, gluconolactone or mixtures thereof.

Also provided are processes for preparing the above-described salt and composition.

DESCRIPTION OF THE DRAWINGS

FIG. 2 shows the infrared absorption spectrum of a typical water-soluble composition when pelleted in potassium bromide.

DETAILED DESCRIPTION

Figure 1:
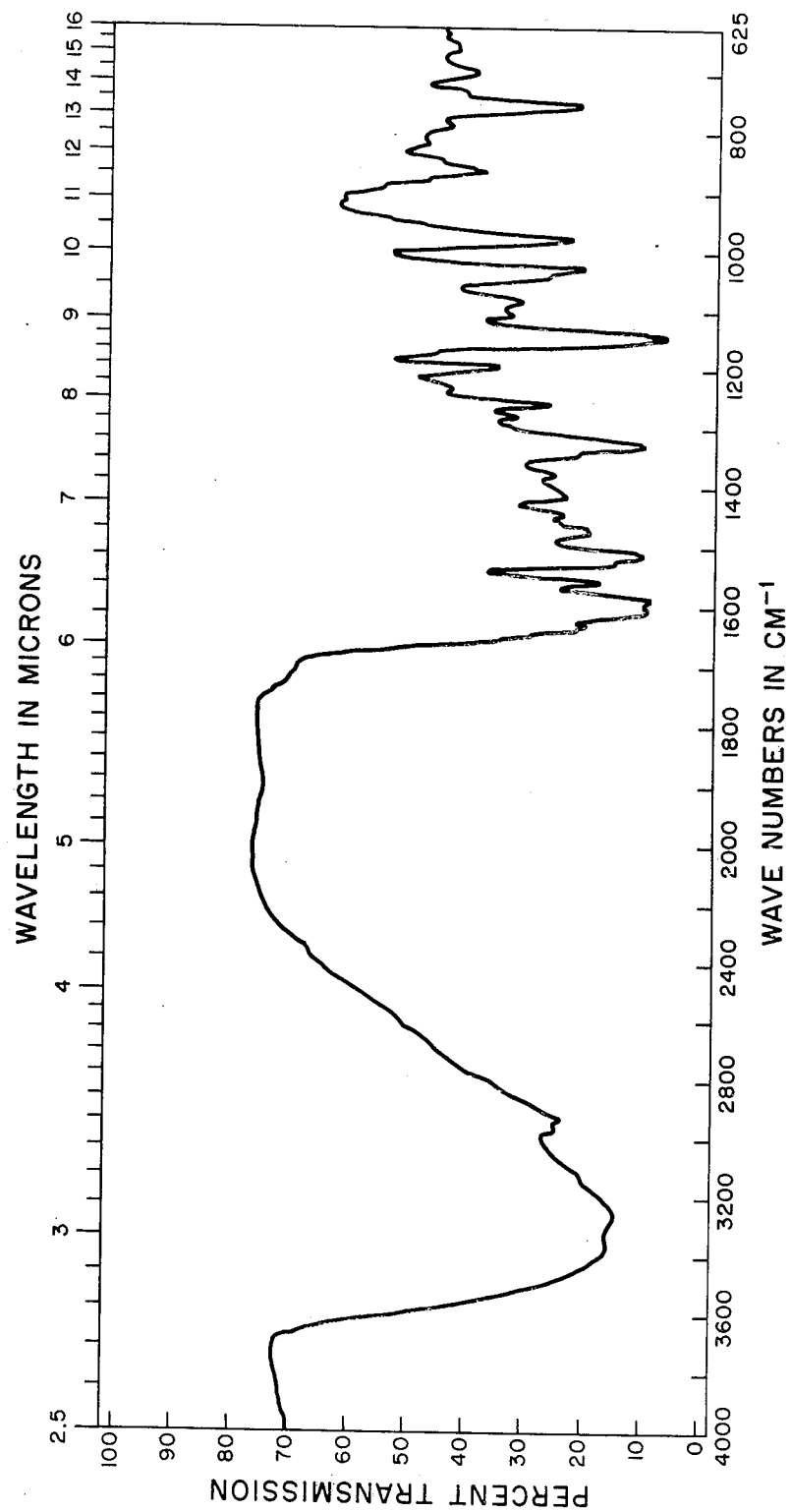
FIG. 1 shows the infrared absorption spectrum of the crystalline gluconate salt when pelleted in potassium bromide.

Many conventional pharmaceutically acceptable acid addition salts of m-AMSA are only slightly soluble in water and are thus unsuited for intravenous administration to human patients. This is evident from literature references to the hydrochloride and methanesulfonate salts as well as from solubility tests carried out by the present inventors on salts such as the levulinate, citrate and lactobionate.

In investigating solubility properties of m-AMSA acid addition salts, we have unexpectedly found that one particular crystalline salt of m-AMSA possesses significantly high water-solubility at room temperature to provide an acceptable intravenous dosage form. Thus, the noval monogluconate salt of m-AMSA provided by the present invention has an aqueous solubility at room temperature of about 25 mg/ml. This gluconate salt has also been found to have acceptable stability, both as a crystalline solid and as an aqueous solution upon reconstitution.

Preparation of the crystalline gluconate salt of m-AMSA is carried out by the steps of (1) forming a solution of m-AMSA and an organic acid (or precursor thereof) selected from the group consisting of gluconic acid (D-gluconic acid), gluconolactone (D-gluconic acid δ-lactone) and mixtures thereof in an inert aqueous polar organic solvent, the molar ratio of organic acid to m-AMSA being from about 1:1 to about 2:1; and (2) crystallizing the desired gluconate salt from the so-produced solution.

The particular inert polar organic solvent used to solubilize the m-AMSA base is not critical and examples of suitable solvents will be readily apparent to those skilled in the art. Preferred solvents are polar alcohols and ketones such as methanol, ethanol, n-propanol, isopropanol, acetone, n-butanol, 2-butanone, n-pentanol, n-hexanol, diethylene glycol, methyl isobutyl ketone, 3-pentanone, etc. A particularly convenient solvent is ethanol. The solvent system should contain a small percentage of water (e.g. ~0.5%) which may either be added to the organic solvent or preferably supplied in the form of aqueous gluconic acid or gluconolactone solution.

The term "organic acid" as used herein and in the claims refers to gluconic acid per se or a precursor thereof which hydrolyzes in aqueous solution to form gluconic acid, e.g. gluconolactone. Gluconic acid is difficult to produce in a well-defined crystalline form and thus commercial gluconic acid is supplied as a 50% aqueous solution. Gluconolactone, on the other hand, is a well-defined crystalline material which may be easily hydrolyzed in aqueous solution to gluconic acid. Because of the availability of crystalline gluconolactone, it is preferred to use gluconolactone as the source of gluconic acid in preparing the gluconate salt. The gluconolactone may be added to an aqueous solution of the polar organic solvent to generate the gluconic acid or may be added to the organic solvent in the form of an aqueous solution.

The temperature at which solution is effected is not critical and may range from the freezing point to the boiling point of the solvent system. Most advantageously temperatures of around room temperature or above are used. It has been found that solubility is maximized if the mixture is brought to reflux temperature.

The gluconic acid or gluconolactone may be employed in molar ratios of about 1 to 2 moles per mole of m-AMSA base. Best quality product, however, has resulted from using equimolar quantities of the m-AMSA and organic acid.

After forming a solution of m-AMSA and acid, it is preferred to carry out a filtration step before allowing crystallization to proceed. Standard crystallization techniques may then be used to obtain the desired gluconate salt. Seed crystals of the gluconate salt may be added to the reaction mixture to induce and/or enhance crystallization. After recovery the crystalline salt is washed (e.g. with ethanol) and dried by conventional procedures. Recrystallization (e.g. from ethanol) may be used to obtain product in a highly purified form.

In another aspect the present invention provides a stable, solid, water-soluble composition suitable upon reconstitution with water or other aqueous vehicle as a stable solution of m-AMSA, said composition comprising a mixture of about one mole of m-AMSA monogluconate salt per one to three moles of an organic acid (or precursor thereof) selected from the group consisting of gluconic acid, gluconolactone and mixtures thereof.

The above-described composition may be employed in the form of either a dry-fill or lyophilized product, but is preferably a lyophilized mixture. The composition may be conveniently and rapidly reconstituted with sterile water or a sterile aqueous vehicle to provide at least a 5 mg/ml true solution of m-AMSA having excellent stability.

Preparation of the water-soluble composition may be conveniently accomplished by a conventional lyophilization procedure. Thus, an aqueous solution of m-AMSA and an excess of gluconic acid or a source of gluconic acid (i.e. an organic acid which hydrolyzes in water to form gluconic acid) is formed, and the solution is then subjected to a standard lyophilization process to obtain the desired solid composition.

The gluconic acid (or equivalent) is used in a molar ratio of about 2-4 moles (most preferably about 2.5 moles) per mole of m-AMSA base. Since as noted above commercial gluconic acid is not available in a well-defined crystalline form, it is preferred to use crystalline gluconolactone as the organic acid. The gluconolactone rapidly hydrolyzes in water to form gluconic acid. During lyophilization gluconic acid is at least partially converted to gluconolactone. The lyophilized product, therefore, comprises a mixture of the monogluconate salt of m-AMSA with from about one to three moles of excess gluconic acid, said acid being partly in the gluconic acid form and partly in the gluconolactone form.

After forming the aqueous solution of m-AMSA and acid, the reaction mixture is preferably filtered before lyophilization. Lyophilization may be carried out in conventional laboratory or industrial lyophilizers. Preferred lyophilization parameters are as follows:
  prefreezing at $-55°$ C.;
  freezing at $-50°$ C. for 2 hours;
  sublimation at $-40°$ C. for about 68 hours at a pressure of about $4\times10^{-2}$ torr;
  drying at $+30°$ C. for about 48 hours.

The crystalline gluconate salt and water-soluble composition provided by the present invention exhibit substantially the same antitumor properties as the prior art m-AMSA forms. Because of their high water-solubility, however, they may be used to prepare clinical dosage forms for intravenous administration which do not contain an undesirable pharmaceutical vehicle such as dimethylacetamide. The salt and composition, moveover, can be used to prepare a single vial dry-fill or lyophilized product for reconstitution with sterile water or a sterile aqueous vehicle. A preferred vehicle for reconstitution of the gluconate salt is aqueous gluconic acid.

The m-AMSA salt and composition of the present invention may be used to prepare oral or non-intravenous parenteral dosage forms as well as the preferred intravenous injectable product. The salt and composition have acceptable stability, both in solid form and in aqueous solution, and have sufficient water-solubility to permit administration of an effective dose of m-AMSA in a relatively small volume of parenteral solution (thus allowing for bolus i.v. injections).

In the treatment of mammalian tumors, the salt and composition of the present invention may be administered either orally or parenterally, but preferably parenterally, in dosages (adjusted for amount of m-AMSA base) and according to regimens previously disclosed in the literature.

The following examples are given in illustration of, but not in limitation of, the present invention.

EXAMPLE 1

Preparation of m-AMSA Monogluconate Salt

Delta gluconolactone (0.89 g.; 0.005 mole) was dissolved in 0.5 ml. of water. m-AMSA base (1.95 g.; 0.005 mole) and 100 ml. of ethanol were added, and the mixture was then refluxed for a short time, i.e. about 5–10 minutes. The resulting solution was allowed to stand overnight whereupon crystalline material separated from solution. The product was recrystallized from 100 ml. of ethanol to give 1.10 g. of crystalline m-AMSA monogluconate salt.

Properties of gluconate salt:

m-AMSA content by U.V.=62.6% (theoretical content is 66.6%);
gluconic acid content by U.V.=36.9%;
gluconolactone content by U.V.=1.1%.

Solubility in water: 30 mg/ml. at 50°-60° C.; 25 mg/ml. at room temperature.

When dissolved in water at a concentration of 7.1 μg/ml., the gluconate salt exhibits ultraviolet absorption peaks at 208 nm (O.D.=0.527), 247.5 nm (O.D.=0.567), 263 nm (O.D. - 0.425) and 412 nm (O.D.=0.121).

FIG. 1 shows the infrared absorption spectrum of the gluconate salt when pelleted in potassium bromide.

EXAMPLE 2

Preparation of m-AMSA Water-Soluble Composition (For preparation of 75 mg. m-AMSA activity vials)

| Formula | Per Vial | Per Liter Batch |
|---|---|---|
| m-AMSA base | 75 mg. | 5 g. |
| gluconolactone (gluconic acid δ-lactone) | 93.46 mg. | 6.23 g. |
| water for injection | q.s. to 15 ml. | q.s. to 1 liter |

Manufacturing Instructions (for 1 liter batch)

(1) Preparation of a 10% solution of gluconolactone:
weigh 10 g. of gluconolactone
with agitation, add the lactone into a glass container containing 80 ml. water for injection. Maintaining agitation until complete solution is obtained.
q.s. to 100 ml. with water for injection
stir 5 min.
This solution is to be used after 24 hours of standing at room temperature.

(2) Weigh out 5 g. of m-AMSA base.

(3) Into a suitable glass container containing 600 ml. of water for injection, add with agitation 25 ml. of the 10% gluconolactone solution.

(4) With strong agitation add slowly the 5 g. of m-AMSA base to the glass container. Maintain agitation for 30 min.

(5) With agitation add 20 ml. of the 10% gluconolactone solution to the reaction mixture. Agitate for 30 min.

(6) Slowly add the remainder of the 10% gluconolactone solution (17.3 ml.) to the reaction mixture. Maintain agitation until complete solution is obtained.

(7) Q.S. to 1 liter with water for injection.

(8) Using nitrogen pressure pass the solution through a 0.22μ filter.

(9) Fill the solution into 30-38 ml. flint glass vials (15 ml. solution per vial). Partially insert red butyl lyophilization stoppers.

(10) Subject vials to freeze drying at following parameters:
prefreezing at −55° C.;
freezing at −50° C. for 2 hours;
sublimation at −40° C. for about 68 hours at a pressure of about $4 \times 10^{-2}$ torr;
drying at +30° C. for about 48 hours.

(11) Stopper the vials under vacuum or nitrogen atmosphere and seal.

(12) To reconstitute, use 20 ml. water for injection per vial.

Properties of Lyophilized Composition.

Reconstitution time with 20 ml. water=4-5 min. pH of solution: 3.65

Analysis of lyophilized product: of 0.172 g. total composition, ~72 mg. m-AMSA, ~93 mg. total gluconic acid (potentiometry) of which ~40 mg. is δ-gluconolactone (gas chromatography). Impurities are below detection limits. % $H_2O$(K.F.)=0.8

Aqueous stability of reconstituted product satisfactory at 24 hours. Loss of potency barely perceptible and no impurities were noted.

When dissolved in water at a concentration of 12.17 μg/ml., the lyophilized composition exhibits ultraviolet absorption peaks at 209 nm (O.D.=0.607), 247.5 nm (O.D.=0.607), 266 nm (O.D.=0.534), 413 nm (O.D.=0.145) and 435 nm (O.D.=0.143).

FIG. 2 shows the infrared absorption spectrum of the lyophilized composition when pelleted in potassium bromide.

We claim:

1. The crystalline gluconate salt of m-AMSA.

2. A stable, solid, water-soluble composition for reconstitution with water or aqueous vehicle as a stable solution of m-AMSA, said composition comprising a mixture of about one mole of m-AMSA gluconate salt per one to three moles of an organic acid selected from the group consisting of gluconic acid, gluconolactone and mixtures thereof.

3. The composition according to claim 2 having about one mole of m-AMSA gluconate salt per 1.5 moles of organic acid.

4. A stable, solid, water-soluble composition for reconstitution with water or aqueous vehicle as a stable solution of m-AMSA, said composition being produced by the steps of
   (1) forming an aqueous solution of m-AMSA and an organic acid selected from the group consisting of gluconic acid, gluconolactone and mixtures thereof, the molar ratio of the organic acid to m-AMSA being from about 2:1 to about 4:1; and
   (2) lyophilizing the so-produced aqueous solution.

5. The composition according to claim 4 wherein about 2.5 moles of organic acid are used per mole of m-AMSA.

6. The composition according to claim 4 or claim 5 wherein the organic acid used is gluconolactone.

7. The composition according to claim 4 wherein the aqueous solution of step (1) is formed by reacting about 5 g. m-AMSA and 6.23 g. gluconolactone per liter of solution.

* * * * *